United States Patent
Naus et al.

(10) Patent No.: US 11,986,264 B2
(45) Date of Patent: *May 21, 2024

(54) SURGICAL MASTER-SLAVE ROBOT

(71) Applicant: PRECEYES B.V., Eindhoven (NL)

(72) Inventors: Gerrit Jacobus Lambertus Naus, Eindhoven (NL); Hildebert Christiaan Matthijs Meenink, Steenderen (NL); Maarten Joannes Beelen, 's-Hertogenbosch (NL); Marc Joseph Dominique De Smet, Mont sur Lausanne (CH)

(73) Assignee: PRECEYES B.V., Eindhoven (NL)

( * ) Notice: Subject to any disclaimer, the term of this patent is extended or adjusted under 35 U.S.C. 154(b) by 697 days.

This patent is subject to a terminal disclaimer.

(21) Appl. No.: 17/141,167

(22) Filed: Jan. 4, 2021

(65) Prior Publication Data
US 2021/0153962 A1   May 27, 2021

Related U.S. Application Data

(63) Continuation of application No. 16/075,821, filed as application No. PCT/EP2017/052103 on Feb. 1, 2017, now Pat. No. 10,905,509.

(30) Foreign Application Priority Data

Feb. 4, 2016   (EP) .................... 16154172

(51) Int. Cl.
*A61B 34/37*   (2016.01)
*A61B 34/00*   (2016.01)
(Continued)

(52) U.S. Cl.
CPC ............. *A61B 34/37* (2016.02); *A61B 34/70* (2016.02); *A61B 90/50* (2016.02); *A61F 9/007* (2013.01);
(Continued)

(58) Field of Classification Search
CPC ......... A61B 34/25; A61B 34/37; A61B 34/70; A61B 90/50; A61B 2090/508; A61F 9/007

See application file for complete search history.

(56) References Cited

U.S. PATENT DOCUMENTS 5,628,732 A   5/1997   Antoon, Jr. et al.
5,957,832 A   9/1999   Taylor et al.
(Continued)

FOREIGN PATENT DOCUMENTS

CN   1457747 A    11/2003
CN   103037799 A   4/2013
(Continued)

OTHER PUBLICATIONS

Uneri, A., et al., "New Steady-Hand Eye Robot With Micro-Force Sensing for Vitroretinal Surgery," Biomedical Robotics and Biomechatronics (BIOROB), 2010 3rd IEEE RAS and EMBS International Conference On, IEEE, Piscataway, NJ, USA, Sep. 26, 2010, pp. 814-819, XP031793378.
(Continued)

*Primary Examiner* — Ashley L Fishback
(74) *Attorney, Agent, or Firm* — Whitestone Law, PLLC

(57) ABSTRACT

Some embodiments are directed to a surgical master-slave robot for use in minimally (or reduced) invasive surgery on a subject. The robot includes an instrument manipulator for mounting of a surgical instrument, and a linkage system for moveably suspending the instrument manipulator. A first linkage component is configured for guiding a first suspension to move along a first movement trajectory. A second linkage component is configured for guiding a second suspension point to move along a second movement trajectory. The first movement trajectory and the second movement trajectory differ and are selected to provide a combined translational and rotational movement of the instrument (Continued)

manipulator which moves the instrument manipulator along a predefined trajectory from a surgical position to a standby position. The robot may provide a stable removal of the instrument manipulator during a surgery as well as sufficient surgeon's workspace after the removal of the instrument manipulator.

19 Claims, 9 Drawing Sheets

(51) Int. Cl.
    *A61B 90/50*     (2016.01)
    *A61F 9/007*     (2006.01)

(52) U.S. Cl.
    CPC ......... *A61B 34/25* (2016.02); *A61B 2090/508* (2016.02)

(56) References Cited

U.S. PATENT DOCUMENTS

| | | |
|---|---|---|
| 6,788,018 B1 | 9/2004 | Blumenkranz |
| 2004/0261179 A1 | 12/2004 | Blumenkranz |
| 2012/0160238 A1 | 6/2012 | Matlock et al. |
| 2012/0245596 A1 | 9/2012 | Meenink |
| 2015/0245875 A1 | 9/2015 | Meenink |

FOREIGN PATENT DOCUMENTS

| | | |
|---|---|---|
| WO | WO95/10218 A1 | 4/1995 |
| WO | WO96/39944 A1 | 12/1996 |
| WO | WO00/30557 A1 | 6/2000 |

OTHER PUBLICATIONS

International Search Report and Written Opinion for PCT Patent App. No. PCT/EP2017/052103 (dated Jun. 26, 2017).

SURGICAL MASTER-SLAVE ROBOT

CROSS REFERENCE TO RELATED APPLICATION(S)

This application is a continuation of U.S. patent application Ser. No. 16/075,821 filed on Aug. 6, 2018, and allowed on Oct. 1, 2020, which is a National Phase Filing under 35 C.F.R. § 371 of and claims priority to PCT Patent Application No. PCT/EP2017/052103, filed on Feb. 1, 2017, which claims the priority benefit under 35 U.S.C. § 119 of European Patent Application No. 16154172.7, filed on Feb. 4, 2016, the contents of each of which are hereby incorporated in their entireties by reference.

BACKGROUND

Some embodiments relate to a surgical master-slave robot for use in minimally (or reduced) invasive surgery which includes an instrument manipulator and a linkage system for moveably suspending the instrument manipulator. Some other embodiments relate to a cannula connector for connecting the instrument manipulator to a cannula.

Robotically assisted surgery with a master-slave system may assist a surgeon in performing a minimally (or reduced) invasive surgery. Typically, the slave system performs the actual surgery, by instrument manipulators which handle surgical instruments. The surgeon remains in control of the instruments by operating a master. A temporarily removal of an instrument manipulator from a surgical position proximate to a subject may be desired, for example, to make sufficient room for the surgeon to perform surgery by hand. In some surgical operations, e.g., eye surgery, the surgeon may need to accesses the subject for manual surgery multiple times during the operation. Thus the temporarily removal of the instrument manipulator from the proximity of the subject for to perform manual surgery and then return of the instrument manipulator back to the surgical position to continue the minimally (or reduced) invasive surgery may be required multiple times during the operation. Due to such repetitions, besides the requirement of providing sufficient room at the surgical position after the temporary removal of the instrument manipulator, a stable and quick removal of the instrument manipulator is often desired. When the removal is repeated multiple times, stability of the removal may, in general, help to avoid damage to the tissue under surgery and also to the robot. In addition, in emergency cases, a quick removal of the instrument manipulator may be particularly advantageous or preferred.

US 20040261179 A1 describes a method and apparatus for the mounting of surgical setup arms to the table pedestal or floor below an operating table. The ceiling-height-mounted robotic arm assembly and below-table-mounted robotic arm assembly may be pre-configured to be ready for surgery while the fixable set-up arms are disposed generally clear of the personnel-usable space adjacent the operating table. The ceiling mounted setup arm is said to include at least one parallelogram-link structure. Each parallelogram may be raised and lowered vertically, with minimal residual force, with gas springs being selected to support the majority of the system weight throughout the range of motion.

A publication titled "Vitreo-retinal eye surgery robot; sustainable precision, 2011, H. C. M. Meenink, PhD Thesis" describes a surgical master-slave robot for use in minimally (or reduced) invasive surgery. The surgical master-slave robot of Meenink includes an instrument manipulator and a parallelogram linkage system for positioning the instrument manipulator. The linkage system is configured to rotationally move the instrument manipulator from a surgical position proximate to a subject to a standby position distal to the subject. During the rotational movement, the instrument manipulator is suspended on a suspension point of the instrument manipulator via a linkage component coupled to the instrument manipulator.

SUMMARY

A disadvantage of the surgical master-slave robot of Meenink is that the instrument manipulator is insufficiently stable during the removal of the instrument manipulator and, moreover, after the removal, the instrument manipulator still remains in the surgeon's workspace of manual surgery through which the surgeon's hands move, or through which instruments are handed to the surgeon.

It would be advantageous to have a surgical master-slave robot which addresses at least one of the above disadvantages.

To better address this concern, a first aspect of some embodiments provides a surgical master-slave robot for use in minimally (or reduced) invasive surgery on a subject, the surgical master-slave robot including:

an instrument manipulator for mounting of a surgical instrument; and a linkage system for moveably suspending the instrument manipulator, the linkage system including:

a first linkage component coupled to the instrument manipulator at a first suspension point of the instrument manipulator;

a second linkage component coupled to the instrument manipulator at a second suspension point of the instrument manipulator;

wherein:

the first linkage component is configured for guiding the first suspension point of the instrument manipulator to move along a first movement trajectory;

the second linkage component is configured for guiding the second suspension point of the instrument manipulator to move along a second movement trajectory; and wherein the first movement trajectory and the second movement trajectory differ and are selected to provide a combined translational and rotational movement of the instrument manipulator which moves the instrument manipulator along a predefined trajectory from a surgical position proximate to the subject to a standby position distal to the subject.

The above measures involve an instrument manipulator for mounting of a surgical instrument. Instrument manipulators for surgical master-slave robots are known in the art per se. The instrument manipulator may be, for example, a mount. The instrument manipulator may be affixed to the robot and thereby take over the tasks of the surgeons hand by handling and manipulating surgical instruments or surgical tools. A surgical instrument may be a specially designed tool or device for performing specific actions of carrying out desired effects during a surgery or operation, such as modifying biological tissues, or to provide access for viewing it. Examples of such surgical instruments include, but are not limited to, forceps, mechanical cutters, coagulation cutters, scissors, injection needles, sealing devices, etc.

The above measures further involve a linkage system for moveably suspending the instrument manipulator. Examples of linkage systems range from the four-bar linkage used to amplify force in a bolt cutter or to provide independent suspension in an automobile, to complex linkage systems in robotic arms and walking machines. In a linkage system, linkage components such as bars (also referred to as links) may be connected to one or more other links by, for example, pin joints (also referred to as hinges), sliding joints, or ball-and-socket joints so as to form a closed chain or a series of closed chains. A linkage component may be connected to a body, e.g. an instrument manipulator, to suspend and/or move the body. The connection point of the body and the linkage component may be referred to as a suspension point. In the present robot, the linkage system includes a first linkage component coupled to the instrument manipulator at a first suspension point of the instrument manipulator. The linkage system further includes a second linkage component coupled to the instrument manipulator at a second suspension point of the instrument manipulator. Linkage systems, also referred to as linkages, are know in the art per se.

It is an insight of the applicants that, upon a temporary removal, sufficient room for a surgeon will be provided while at the same time the instrument will remain compact and close to the surgeon to be returned when desired, without restricting the surgeon's performance. This effect is achieved namely by providing the configuration and arrangement of the instrument manipulator and the linkage system and their coupling as claimed which enable a combined translational and rotational movement of the instrument manipulator during a repositioning. As opposed to some embodiments, in the related art robot of Meenink the instrument manipulator is only rotated upon a temporary removal of the instrument manipulator which will result in an insufficient working space. Rotating the system further away would solve this problem, but may require more room for the system to rotate through and will make the return of the instrument manipulator to the surgical area more difficult. This problem of the related art robot is solved in an inventive way by the applicants, by arranging the linkage system so that a selected translational movement, which may refer to a rigid displacement without a rotation, is added to a selected rotational movement which enable a flexible in-plane as well as spatial movement of the instrument manipulator in any desired direction along a predefined trajectory. Here, the rotational movement may be established by each suspension point being guided along a differently shaped motion trajectory, whereas same-shaped motion trajectories provide only translation.

For example, the linkage system may be arranged to enable repositioning of the instrument manipulator by removing the instrument manipulator by a small-radius rotation and then moving the instrument manipulator by a translational-rotational movement to a position outside the surgeon's working space, e.g., below the working space area. As such, sufficient space will be provided for the surgeon to manually perform surgical tasks while at the same time the robot remains compact and sufficiently close to the surgeon for convenient return of the robot back to the surgical area when desired.

In addition to the above advantage, the applicants have the insight that by the arrangement and the configuration of the instrument manipulator and the linkage system of some embodiments, the instrument manipulator is suspended on two suspension points during the movement. As a result, the robot and the instrument manipulator will remain stable during the temporal movement. As such, the system may advantageously be less vulnerable when moved away. Moreover, compared to a less robust and stable system such as that with one suspension point, the system with increased stability may help to avoid inducing damage to the tissue under surgery upon the removal. Moreover, by being guided along a predefined trajectory, the movement of the instrument manipulator may be constrained to the trajectory, which facilitates assuming the surgical position from the standby position and vice versa. As such, the instrument manipulator may be easily moved from its standby position along the predefined trajectory to the surgical position, e.g., to easily (re)connect to a trocar. It is noted that the robust design of the robot according to some embodiments may be advantageous not only for the removal of the instrument manipulator but also for accurate return and repositioning of the instrument manipulator back to the surgical position to resume the robotic surgery. Stabilized instrument positioning may also enhance dexterity on surgical tasks and some embodiments, as such, discloses a more robust surgical master-slave robot for use in minimally (or reduced) invasive surgery.

Optionally, the movement of the instrument manipulator causes a tip of a distal end of the instrument manipulator to move along a third movement trajectory, wherein an end portion of the third movement trajectory proximate to the subject is oriented in a direction perpendicular to a surgical entry surface of the subject. This is advantageous in that the removal of the instrument manipulator from an entry site of the surgical instrument on the subject may be safer for the patient when the instrument manipulator is removed in a substantially perpendicular direction. Deviation above a threshold, e.g., 22.5° degrees, from this perpendicular direction may damage a tissue of the subject upon removal of the instrument manipulator. For example, when the instrument manipulator is coupled to a cannula at a proximal end, substantial deviations of the removal of the instrument from substantially perpendicular orientation, e.g., parallel to a central symmetry axis of the cannula, may exert lateral forces to the cannula which may be harmful for the patient. It is further noted that directions within the range of 90±0 degrees, 90°±2° degrees, 90°±5° degrees, 90°±10° or 90°±22.5° degrees may be considered substantially perpendicular directions for obtaining a safe removal of the instrument manipulator.

Optionally, the standby position is located laterally sideways with respect to a sagittal plane of the subject and the linkage system is configured for guiding the instrument manipulator laterally sideward with respect to the sagittal plane during the movement from the surgical position to the standby position. Such repositioning of the instrument manipulator may advantageously result in the removal of the instrument manipulator from the area directly above the subject which may be an important area for the surgeon, for example, in an emergency or to perform regular manual tasks during operations.

Optionally, the standby position is located lower than the subject and the linkage system is configured for guiding the instrument manipulator downward with respect to a coronal plane of the subject during the movement from the surgical position to the standby position. Advantageously, such repositioning of the instrument manipulator may provide further room to the surgeon to have access to the area around the subject and the surgical entry site. For example, repositioning of the instrument manipulator below a subject may provide sufficient space for a surgical assistant to give surgical tools to the surgeon. It is noted that repositioning may, in general, refer to a change in position, e.g., changing from the surgical position to the standby position or vise versa.

Optionally, the surgical master-slave robot includes a release mechanism for holding and releasing the instrument manipulator at the surgical position; and the movement of the instrument manipulator is obtained as a result of force acting upon the instrument manipulator when the release mechanism releases the instrument manipulator, the force being generated by gravity and/or a preloaded spring. Such gravity and/or preloaded spring actuated removal of the instrument manipulator is advantageous in that it makes the removal more convenient as a surgeon or other personnel do not have to waste energy to accurately reposition the instrument manipulator every time the removal may be required. This would be particularly advantageous when the instrument manipulator may be required to be removed multiple times during an operation. With such gravity and/or a preloaded spring actuation, a separate electrical actuator, which may fail in case of, e.g., power failure, may not be required. As such, the release mechanism may be more robust and reliable.

Optionally, the release mechanism includes a hook, a lock arm pin, and a release actuator, wherein the hook is arranged and configured for gripping the lock arm pin; the lock arm pin being connected to one of the first linkage component, the second linkage component or the instrument manipulator via a lock arm, and the release actuator is arranged and configured for releasing the hook from the lock arm pin. By moving the hook toward the lock arm pin, the hook may simply grip the lock arm pin and thereby lock the mechanism, and the lock may be simply released by activating the release actuator, e.g., by way of pushing a handle of the release actuator. As such, the described locking mechanism may enable a quick and convenient release and repositioning of the instrument manipulator when desired. Furthermore, such locking mechanism may enable an accurate return of the instrument manipulator back in place to the surgical working space to continue the operation tasks by the surgical instrument when desired.

Optionally, the linkage system is provided with a manual actuation handle for enabling a user to manually actuate the linkage system so as to move the respective suspension point of the instrument manipulator along the respective movement trajectory. This may allow convenient control of a user of the movement of the instrument manipulator when desired. By actuating the linkage system via the handle, an easy control of the function of the linkage system may be advantageously obtained.

Optionally, the surgical master-slave robot includes an actuator for actuating the linkage system so as to move the respective suspension point of the instrument manipulator along the respective movement trajectory. Including the actuator may enable an automatic actuation of the linkage system and thereby an automatic control of the movement of the instrument manipulator.

Optionally, at least one of the first linkage component and the second linkage component includes or is constituted by a slider for sliding along a guide shaped to establish the respective movement trajectory. Advantageously, the guide may simply provide the respective trajectory for the slider and the movement may be thus simply performed by sliding the slider along the guide. Using sliders in the linkage system may be, in general, advantageous in obtaining a smooth and guided movement of the suspension points in the desired movement trajectories. A slider may be, for example, a carriage which may slide on a track.

Optionally, at least one of the first linkage component and the second linkage component is a rod member rotatable about a rotation point and a rotation of the at least one of the first linkage component and the second linkage component about the rotation point provides the movement of the respective suspension point along the respective movement trajectory. Advantageously, various movement trajectories may be achieved simply by using rod members with different lengths.

Optionally, one or both of the first movement trajectory and the second movement trajectory are arc-shaped movement trajectories. Although the movement trajectories may have any shape, arc-shaped movement trajectories may advantageously enable a desired rotation of the instrument manipulator such that an optimal route for the movement of the instrument manipulator may be selected.

Optionally, the surgical master-slave robot further includes a cannula connector for coupling to a cannula, wherein the cannula provides an opening at the surgical entry surface of the subject for the surgical instrument to enter an interior of the subject, and wherein the cannula connector:

is coupled to the instrument manipulator at a proximal end;

includes a through passage for allowing the surgical instrument to pass through the through passage; and is shaped to fit a shape of the cannula so as to establish a releasable coupling with the cannula which releases when the instrument manipulator moves in the direction perpendicular to a surgical entry surface of the subject.

Cannulas are known in the art per se. The cannulas may enable easy switching between surgical instruments, making use of the same entry point without unnecessarily puncturing a tissue of the subject at multiple places. Furthermore, the cannulas may provide a 'safety boundary' between the surgical instruments and the tissue, protecting the tissue. By using a cannula connector between the instrument manipulator and the cannula that is aligned with a longitudinal axis of the surgical instrument, sideways forces on the surgical instrument may be prevented as the cannula connection may force the cannula to be aligned with the instrument manipulator and thereby with the surgical instrument.

Optionally, the cannula has a conical shape and wherein the cannula connector is conically shaped to fit the conical shape of the cannula. The conical shape may allow the instrument manipulator with the cannula connector to be easily positioned onto and aligned with the cannula. The angle of the conical shape may be such that the cannula may not rotate underneath the cannula connector such as a ball joint would. Furthermore, the angle of the conical shape may be such that the cannula may be loosened easily when the instrument manipulator is excluded away from the area for surgery. This may be particularly advantageous when a quick release may be required during the operation, e.g., due to emergency. It is also advantageous when the removal of the instrument manipulator is to be repeated multiple times during the surgery, e.g., to allow a manual surgery by the surgeon.

It is noted that the conical shape may allow the instrument manipulator to be put in place, even when the cannula is not aligned with the cannula connector. The cannula connector may guide and rotate the cannula such that the cannula aligns when the instrument manipulator is introduced.

Optionally, the cannula and the cannula connector are rigidly coupled. Sufficiently stiff coupling may ensure sufficient stability and reliability of the connections between the cannula and the cannula connector and may minimize sideways deflections resulting from interaction forces.

A further aspect of some embodiments provides a cannula connector as described above.

It will be appreciated by those of ordinary skill in the art that two or more of the above-mentioned embodiments, implementations, and/or aspects may be combined in any way deemed useful.

BRIEF DESCRIPTION OF THE DRAWINGS

These and other aspects of some embodiments are apparent from and will be elucidated with reference to the embodiments described hereinafter. In the drawings.

DETAILED DESCRIPTION OF EXEMPLARY EMBODIMENTS

Figure 1A:
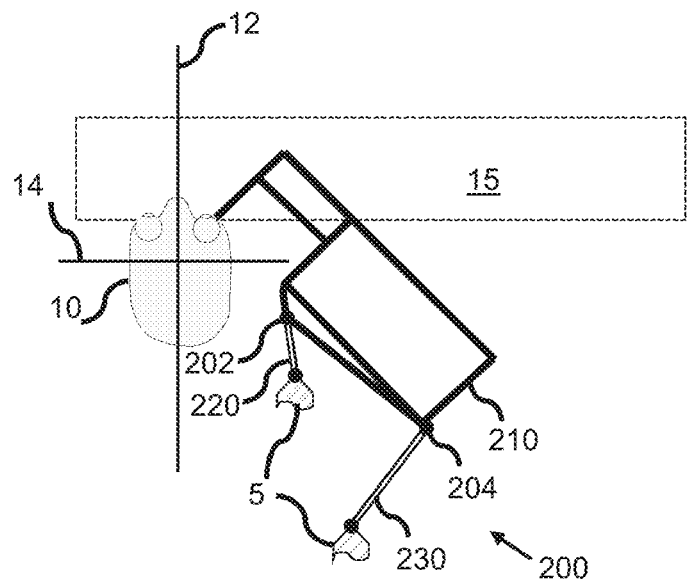
FIG. 1a shows a configuration of a linkage system for moveably suspending an instrument manipulator of a surgical master-slave robot.

It this section, it should be noted that for the sake of explanation, the entire robot has not been shown and some features of the robot, e.g., the linkage system and the movement of the instrument manipulator are explained in details. It is noted that the images show the instrument manipulator to operate on a right eye. For surgery on a left eye, the instrument manipulator may be positioned on the left side of a patient. In case of the left eye surgery, movements described herein may be mirrored with respect to the sagittal plane of the patient. It is noted that, in general, other tissues and organs may be the subject of the surgery and the robot is not limited to be used only in eye surgery. FIG. 1a shows a configuration of a linkage system 200 for moveably suspending an instrument manipulator 210 of a surgical master-slave robot. It is noted that the linkage system 200 and the instrument manipulator 210 are shown schematically and a cut through view in a transverse plane is shown. The linkage system 200 includes a first linkage component 220 coupled to the instrument manipulator at a first suspension point 202 of the instrument manipulator 210. The first linkage component 220 may be configured for guiding the first suspension point 202 of the instrument manipulator 210 to move along a first movement trajectory. The linkage system 200 further includes a second linkage component 230 coupled to the instrument manipulator 210 at a second suspension point 204 of the instrument manipulator 210. The second linkage component 230 may be configured for guiding the second suspension point 204 of the instrument manipulator 210 to move along a second movement trajectory.

Figure 1B:
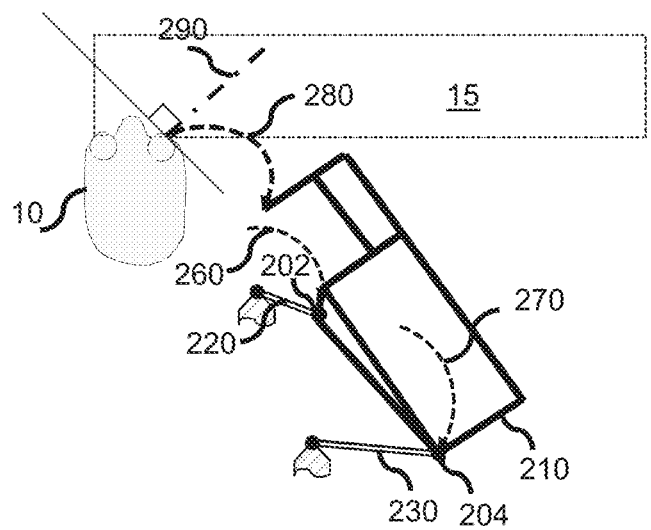
FIG. 1b shows a translational and rotational movement of the instrument manipulator obtained by rotation of a first rod member and a second rod member in a clockwise of rotation.

FIG. 1b shows a translational and rotational movement of the instrument manipulator 210 obtained by rotation of a first rod member 220 and a second rod member 230 in a same direction of rotation. The first rod member 220 may be configured for guiding the first suspension point 202 of the instrument manipulator 210 to move along the first movement trajectory 260. The second linkage component 230 may be configured for guiding the second suspension point 204 of the instrument manipulator 210 to move along the second movement trajectory 270. The suspension point may be a point which couples the instrument manipulator 210 to the linkage system 200 by, for example, bolts and nuts, a hinge, a shaft, etc. In the illustrated configuration, the first rod member 220 may be initially in almost upright position, and the second rod member 230 may be in an angle of about 60°. Here and in the following, the angles are described with respect to 0° corresponding to a 3 o'clock position and 90° corresponding to a 12 o'clock position, i.e., denoting a counterclockwise rotation.

Both rod members 220,230 may rotate clockwise until the second rod member is substantially horizontal. With this configuration, a distal tip of the instrument manipulator or surgical instrument may be repositioned, for example, about 75 mm outwards and 70 mm downwards, moving the instrument manipulator 210 out of the surgeon's workspace 15 in a compact way.

It is noted that, with the claimed arrangement and configuration, upon a temporarily removal of the instrument manipulator, sufficient room for a surgeon may be provided while at the same time the instrument may remain compact and close to the surgeon to be returned when desired, without restricting the surgeon's performance. This effect may be achieved namely by combining translational and rotational movement of the instrument manipulator during the removal.

It is further noted that the first movement trajectory and the second movement trajectory differ and are selected to provide a combined translational and rotational movement of the instrument manipulator 210 from a surgical position proximate to a subject 10 to a standby position distal to the subject 10.

The standby position may be located lower than the subject 10 out of a surgeon's workspace 15 and the linkage system 240 may be configured for guiding the instrument manipulator 210 downward with respect to a coronal plane of the subject during the movement from the surgical position to the standby position. The standby position may be located laterally sideways with respect to a sagittal plane of the subject and the linkage system 240 may be configured for guiding the instrument manipulator 210 laterally sideward with respect to the sagittal plane during the movement from the surgical position to the standby position.

Figure 1C:
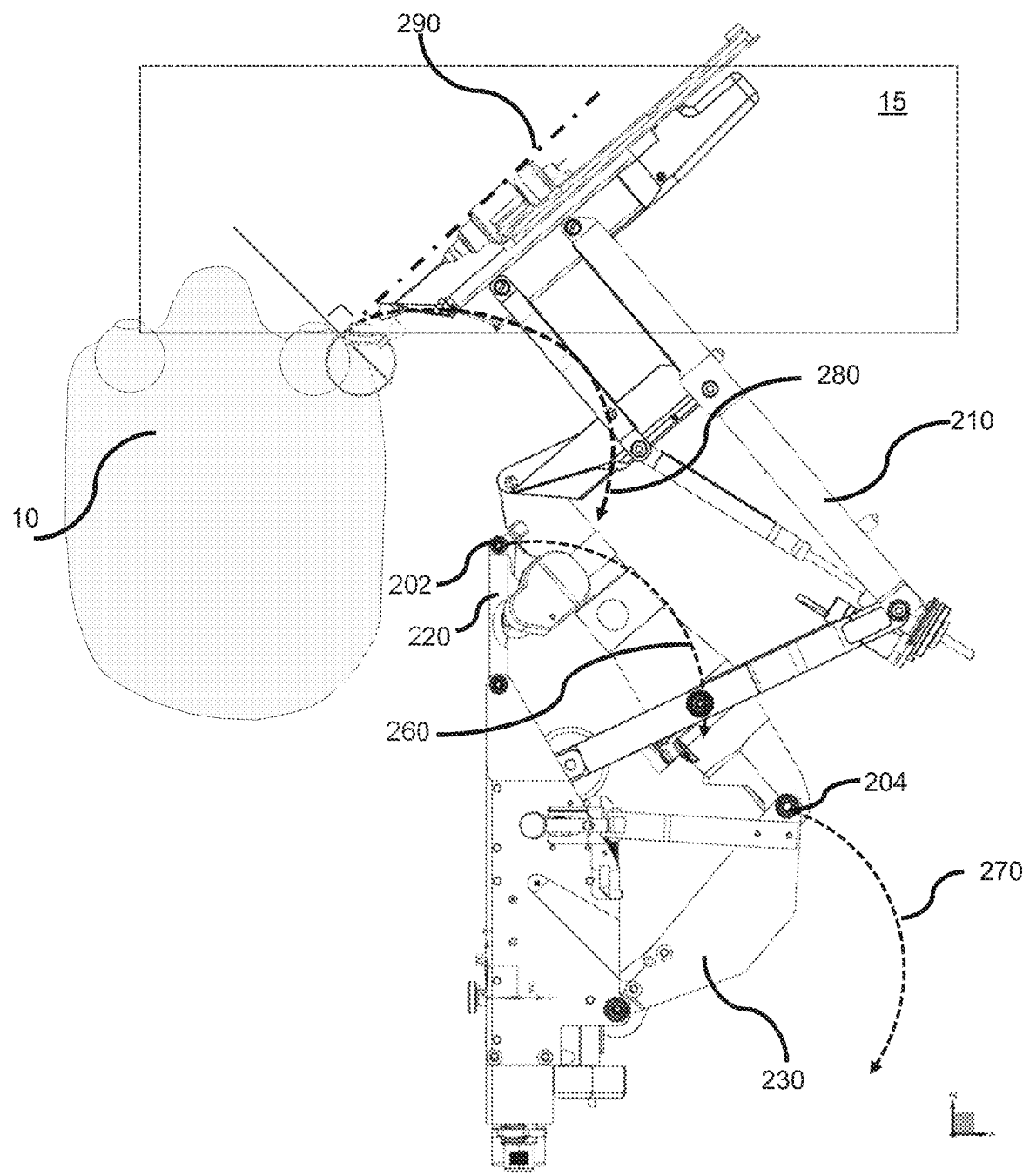
FIG. 1c shows an example of an instrument manipulator and the linkage system of the surgical master-slave robot of FIGS. 1a-b.

FIG. 1c shows an example of the instrument manipulator and the linkage system of the surgical master-slave robot 100 of FIGS. 1a-b. It is noted that the same reference numerals in FIG. 1c and FIGS. 1a-c refer to the same corresponding components.

It is noted that FIGS. 1a-c, as well as FIGS. 2a-5b, show a transverse view of the robot and the subject in a transverse plane. For further clarification of the movement of the instrument manipulator with respect to the subject 10 a sagittal plane 12 and a coronal plane 14 of the subject 10 are indicated in FIG. 1a. It is further noted that the linkage system may be coupled to a base 5 of the surgical robot which is schematically shown in FIG. 1a.

FIGS. 2a-5b, show alternative arrangements and configurations of the linkage system and the instrument manipulator. Same or similar effects and results provided by the arrangement and configuration of FIG. 1 may be achieved.

Figure 2A:
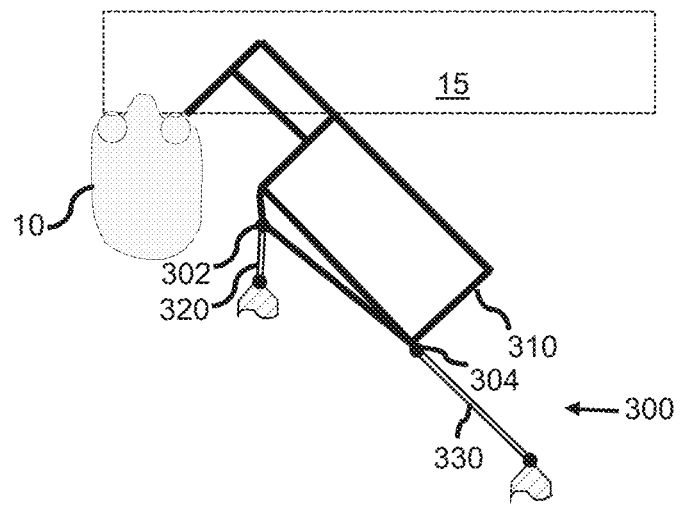
FIG. 2a shows another configuration of a linkage system for moveably suspending an instrument manipulator.
Figure 2B:
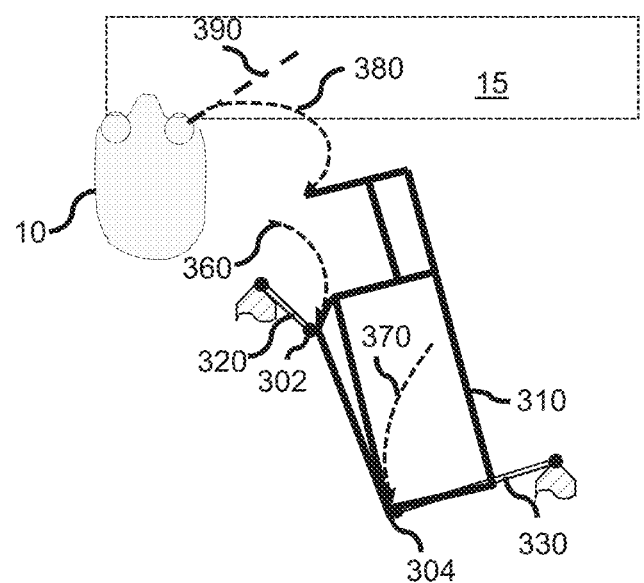
FIG. 2b shows a translational and rotational movement of the instrument manipulator obtained by rotation of a first rod member and a second rod member in opposite directions of rotation.

FIG. 2a shows another configuration of a linkage system 300 for moveably suspending an instrument manipulator 310. FIG. 2b shows a translational and rotational movement of the instrument manipulator 310 obtained by rotation of a first rod member 320 and a second rod member 330 in opposite directions of rotation. The first rod member 320 may be configured for guiding the first suspension point 302 of the instrument manipulator 310 to move along the first movement trajectory 360. The second rod member 330 may be configured for guiding the second suspension point 304 of the instrument manipulator 310 to move along the second movement trajectory 370. In the illustrated configuration, the first rod member 320 may be, for example, in almost upright position and the second rod member 330 in an angle of approximately 135°. The first rod member 320 may rotate clockwise, while the second rod member counterclockwise.

Figure 3A:
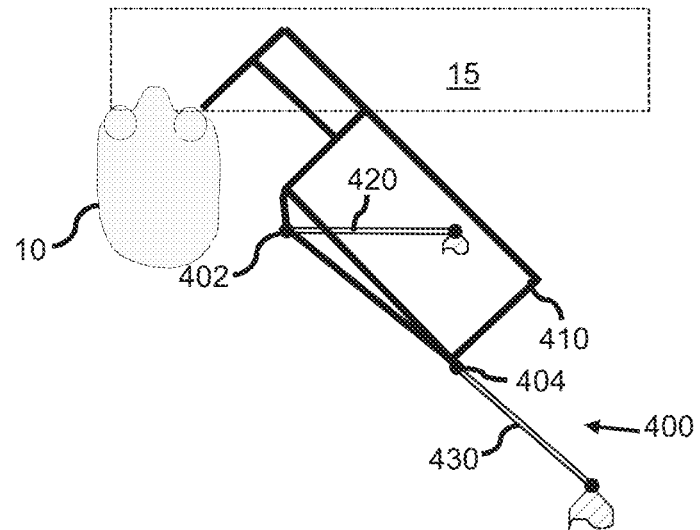
FIG. 3a shows another configuration of a linkage system for moveably suspending an instrument manipulator.
Figure 3B:
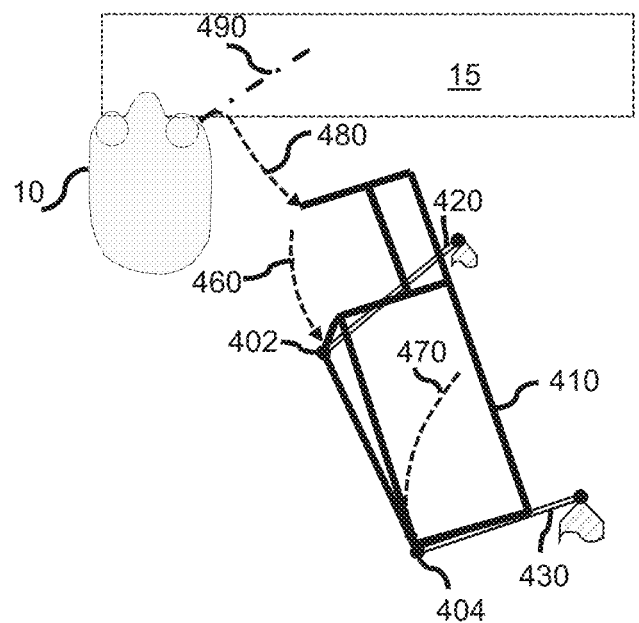
FIG. 3b shows a translational and rotational movement of the instrument manipulator obtained by rotation of a first rod member and a second rod member in a counterclockwise direction of rotation.

FIG. 3a shows another configuration of a linkage system 400 for moveably suspending an instrument manipulator 410. FIG. 3b shows a translational and rotational movement of the instrument manipulator 410 obtained by a rotation of a first rod member 420 and a rotation of a second rod member 430 in a same direction of rotation. In the illustrated configuration, the first rod member 420 may be, for example, in horizontal orientation and the second rod member in an angle of approximately 135°. Both the first rod member and the second rod member may rotate counterclockwise.

Figure 4A:
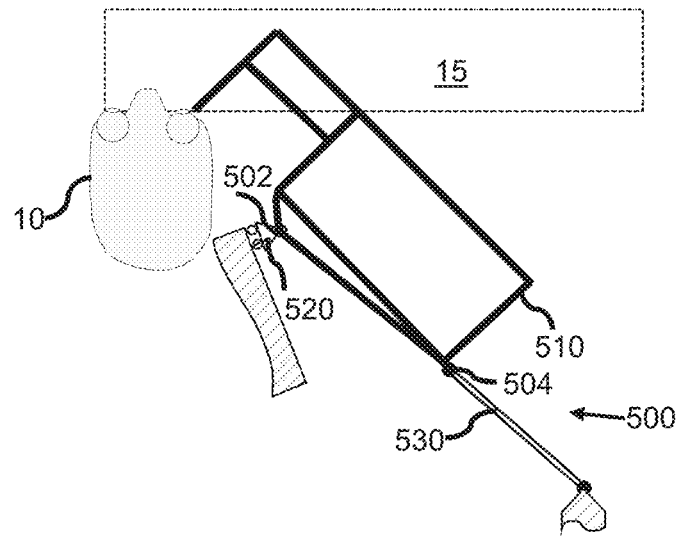
FIG. 4a shows another configuration of a linkage system for moveably suspending an instrument manipulator, wherein the first linkage component is a slider and the second linkage component is a rod member.
Figure 4B:
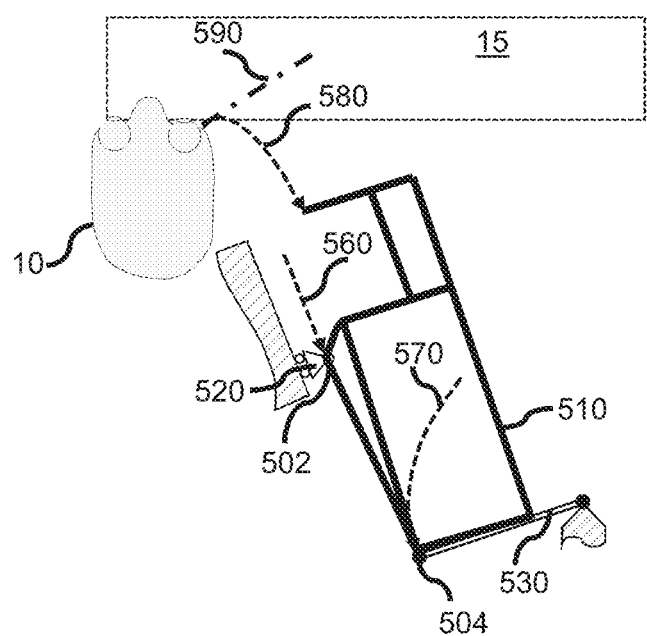
FIG. 4b shows a translational and rotational movement of the instrument manipulator obtained by a rotation of the rod member and sliding of the slider along a substantially straight path.

FIG. 4a shows another configuration of a linkage system 500 for moveably suspending an instrument manipulator 510, wherein the first linkage component is a slider 520 and the second linkage component is a rod member 530. FIG. 4b shows a translational and rotational movement of the instrument manipulator 510 obtained by sliding of the slider 520 for moving a first suspension point 502 along a substantially straight movement trajectory 560 and by a rotation of the second rod member 530 for moving a second suspension point 504 along a second curved or arc-shaped movement trajectory 570.

Figure 5A:
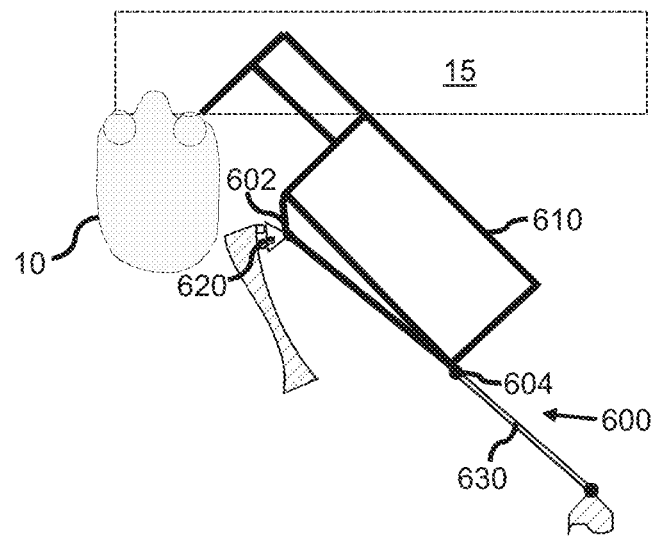
FIG. 5a shows another configuration of a linkage system for moveably suspending an instrument manipulator, wherein the first linkage component is a slider and the second linkage component is a rod member.
Figure 5B:
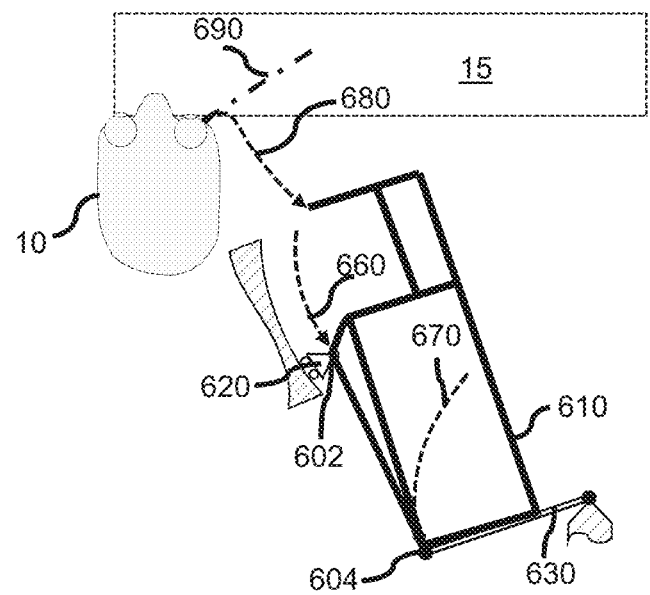
FIG. 5b shows a translational and rotational movement of the instrument manipulator obtained by a rotation of the rod member and sliding of the slider along a curved path.

FIG. 5a shows another configuration of a linkage system 600 for moveably suspending an instrument manipulator 610, wherein the first linkage component is a slider 620 and the second linkage component is a rod member 630. FIG. 5b shows a translational and rotational movement of the instrument manipulator 610 by a rotation of the rod member 630 and by sliding of the slider 620 along a curved path for moving a second suspension point 604 along a second curved or arc-shaped movement trajectory 670.

It is noted that in the illustrated configurations of FIGS. 1a-5b, movement of the instrument manipulator 210, 310, 410,510, 610 may cause a tip of the instrument manipulator and/or a tip of the surgical instrument coupled to the instrument manipulator to move along a third movement trajectory 280, 380, 480, 580, 680. An end of the third movement trajectory proximate to the subject 10 may be in a direction 290, 390, 490, 590, 690, 790 substantially perpendicular to a surgical entry surface of the subject 10. It is noted that in the illustrated configuration of FIGS. 1a-5b, the tip of the surgical instrument may be assumed to be substantially close to a tip of the instrument manipulator and hence surgical instrument is not separately indicated here. In general, however, there might be any desirable distance between the tip of the surgical instrument and the tip of the instrument manipulator.

It should be noted that in general, 2D or 3D configurations other than those illustrated herein may be possible for obtaining a desired movement of the instrument manipulator.

It is further noted that the movement of the instrument manipulator may be obtained as a result of a force, e.g. gravity force and/or spring force, acting upon the instrument manipulator when desired, e.g. when a release mechanism releases the instrument manipulator. In a further example, at least one of the first linkage component and the second linkage component may be provided with a manual actuation handle for enabling a user to manually actuate the linkage system so as to move the respective suspension point of the instrument manipulator along the respective movement trajectory. Various types of handles are known in the art per se. The handle may include a handgrip. It is noted that such an actuation handle may be used to put the instrument manipulator back in place at the surgical position by, e.g., pushing the instrument against gravity. In a further example, the surgical master-slave robot may also include an actuator for actuating the linkage system so as to move the respective suspension points of the instrument manipulator along the respective movement trajectory.

Figure 6A:
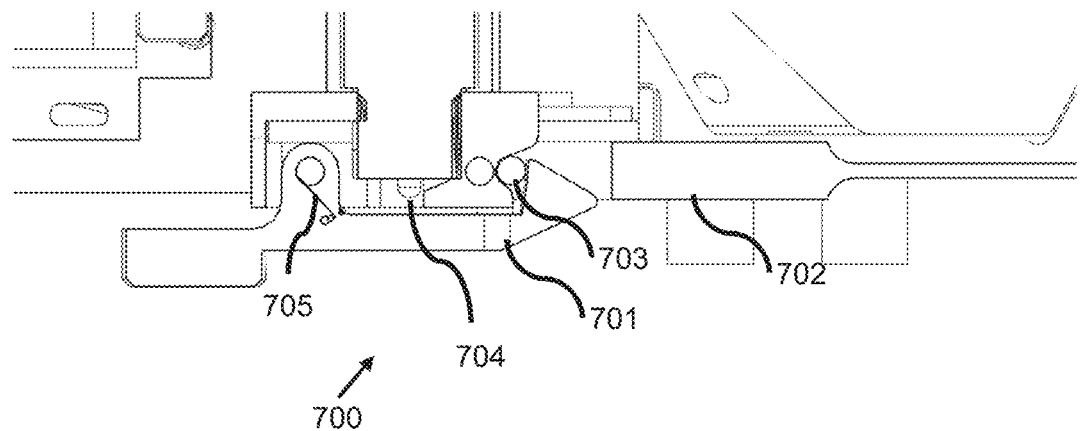
FIG. 6a shows a release mechanism for holding and releasing the instrument manipulator.
Figure 6B:
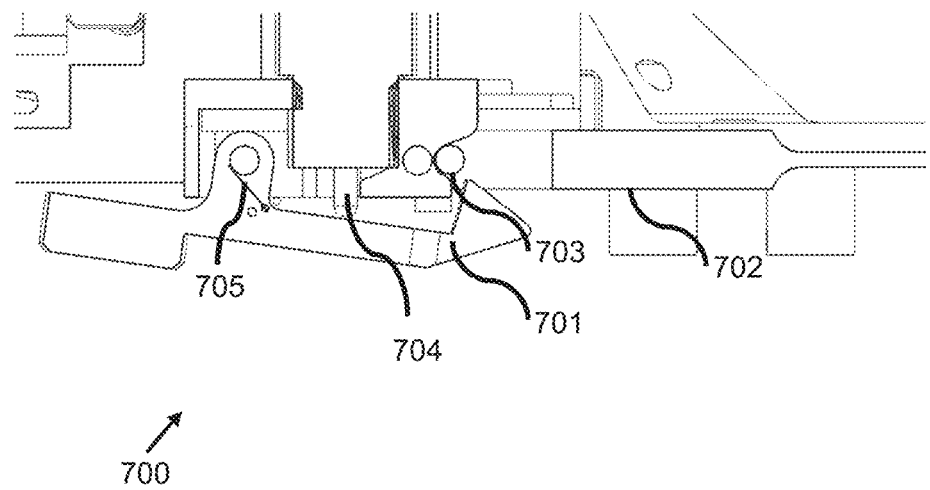
FIG. 6b shows the release mechanism when a release actuator releases a hook of a quick release lock and thereby releases the instrument manipulator via a lock arm.

FIG. 6a shows a release mechanism 700 for holding and releasing the instrument manipulator at a surgical position. The release mechanism may be affixed to the robot (not shown) and may be coupled to the instrument manipulator. By use of the release mechanism 700, the instrument manipulator may be allowed to be released and then move sideways. The release mechanism 700 may include a hook 701, a lock arm pin 703, and a release actuator 704. The hook 701 may be arranged and configured for gripping the lock arm pin 703. It is noted that the hook may also be released manually. The lock arm pin may be connected to one of the first linkage component, the second linkage component or the instrument manipulator via a lock arm 702. The release actuator 704 may be arranged and configured for releasing the hook 701 from the lock arm pin 702. FIG. 6b shows the release mechanism 700 when the release actuator 704 releases the hook 701 and thereby releases the instrument manipulator via the lock arm 702. When released, a drive torque may put the instrument manipulator into motion. Such torque may be applied passively by, e.g., use of storage of potential energy, via either a preloaded torsion spring or by the instrument manipulator's center of gravity. It is noted that the hook 701 may be preloaded via a spring 705 so that an engagement between the hook 701 and the arm lock pin 703 may be enabled when the lock arm 702 advances towards the quick release lock. When locked, the pin of the lock arm may be fixated, using a three-point connection further held in place by the hook 701. This may enable the instrument manipulator to be repositioned back into place with high accuracy. It is noted that the robot may include an actuator (not shown) for actuating the linkage system for repositioning of the instrument manipulator.

Figure 7A:
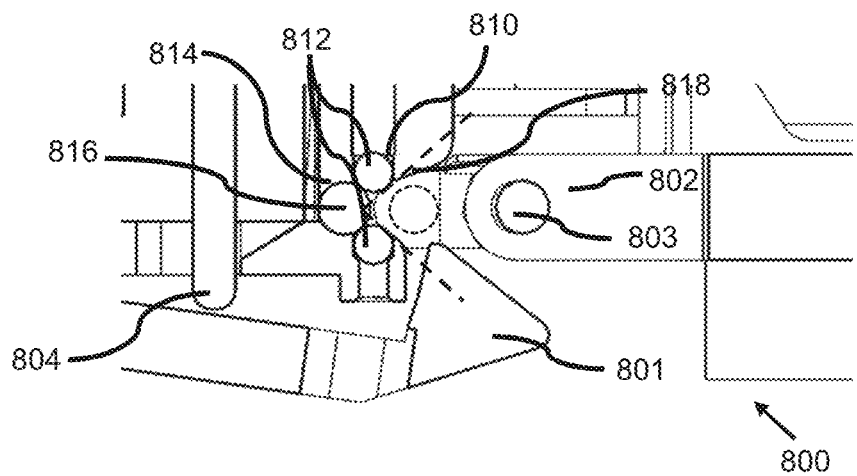
FIG. 7a shows an example of a configuration and construction of a release mechanism.

FIG. 7*a* shows an example of a configuration and construction of a release mechanism 800. The release mechanism 800 may include a first bore 810 in which two bearing balls 812 are positioned. The release mechanism 800 may further include a second bore 814 in which a reference pin 816 may be placed orthogonally and slightly offset. The bearing balls 812 may force against the reference pin 816, and as such, the bearing balls 812 may be precisely located. The bearing balls 812 may form a V-shaped reception 818 of a lock arm pin 803 of a lock arm 802. The V-shaped reception 818 may enable an accurate repositioning of the instrument manipulator. When locking, the lock arm pin 803 may be engaged into the V-shaped reception 818. The lock arm pin 816 may be enclosed by a release hook 801 and thus a three point constraint may be realized that may constrain the lock arm 802 in an X-Y plane only. The lock arm 802 may include a leaf spring or have a leaf spring shape (not shown) providing a compliance so as to enable the lock arm pin 803 to slide all the way into the V-shape reception 818. The bearing balls 812 and the pins 803, 816 may be made of hardened steel.

Figure 7B:
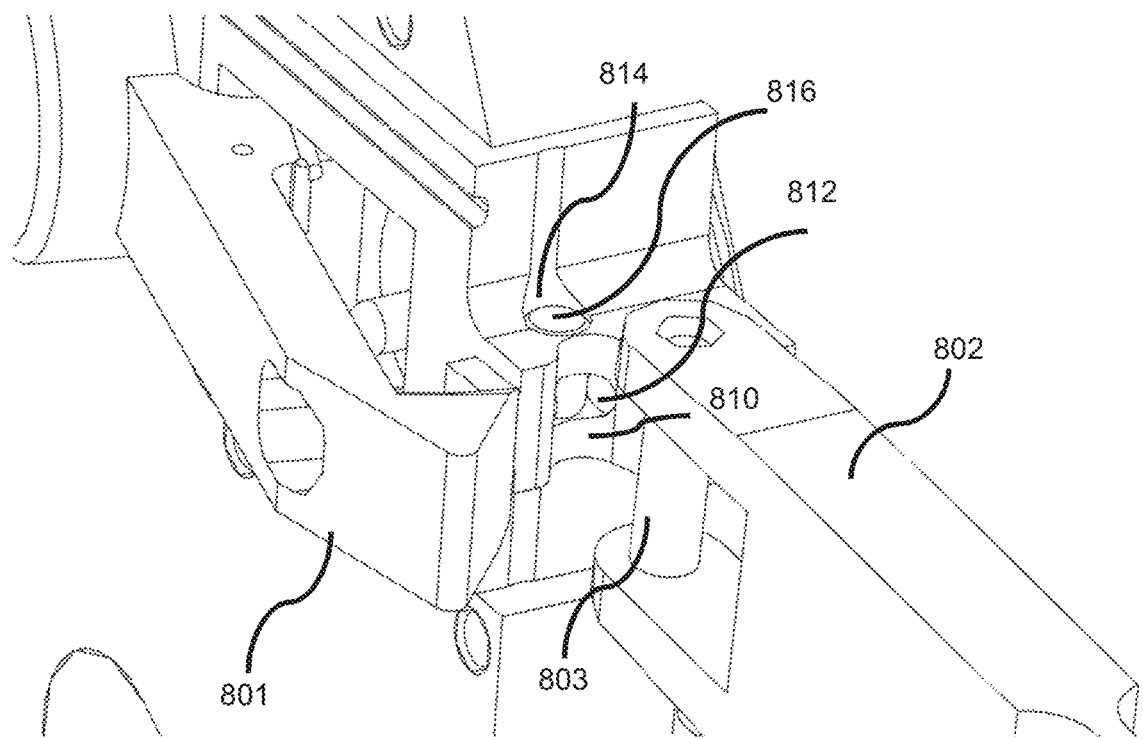
FIG. 7b shows a 3D isometric view of the release mechanism.

FIG. 7*b* shows a 3D isometric view of the release mechanism 800 of FIG. 7*a*.

Figure 8:
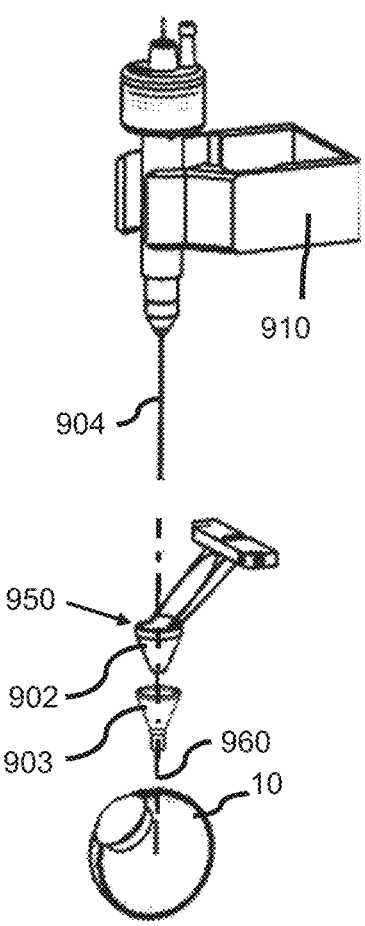
FIG. 8 shows a cannula connector for coupling to a cannula, the cannula connector providing a through passage for a surgical instrument.

FIG. 8 shows another aspect of the claimed surgical robot, namely a cannula connector 902 for coupling to a cannula 903, the cannula connector 902 providing a through passage 950 for a surgical instrument 904 to enter an interior of a tissue, e.g., any eye of a subject for, e.g., eye surgery. In The cannula 903, also known as trocar in some surgical applications, may have on the proximal end an interface to the cannula connector 902 and on the distal end a tube that may be placed in an incision, e.g., the sclera in eye surgery. For example, in eye surgery, the cannula 903 may provide an opening or access point for vitreoretinal instruments to enter the eye. During surgery, multiple cannulas may be used, e.g., one for an infusion, one for a light fiber and one for an articulated instrument). The surgeon may use a microscope to look through the pupil inside the eye, seeing the surgical instrument tips.

The cannula connector 902 may be coupled at a proximal end to an instrument manipulator 910 of a surgical robot. For example, the cannula connector 902 may be coupled to the instrument manipulator 210 of the surgical robot 100 of FIG. 1*c*. The cannula connector 902 may be shaped to fit a shape of the cannula 903 so as to establish a releasable coupling with the cannula 903 which releases when the instrument manipulator 910 moves away from an entry surface on the eye 10 of the subject in a substantially perpendicular direction 960. The cannula 903 and the cannula connector 902 may be made of medical grade materials: such as a selective group of stainless steel, titanium or plastics such as PEEK.

It is noted that in an example, the manipulator may be pushed onto the cannula with a predefined force. This force may be actively measured using a force sensor inside the cannula connector. In a further example, active mechanical clamping and releasing of the cannula may be used. When removing the instrument manipulator away from the area for surgery, the cannula may be loosening automatically. It is noted that active magnets may be also used which may be switched on and off automatically, to connect/disconnect the cannula to the cannula connector. Vacuum may be also used to suck to cannula to the cannula connector.

It should be noted that the above-mentioned embodiments illustrate rather than limit the presently disclosed subject matter, and that those of ordinary skill in the art will be able to design many alternative embodiments without departing from the scope of the appended claims. In the claims, any reference signs placed between parentheses shall not be construed as limiting the claim. Use of the verb "include" and its conjugations does not exclude the presence of elements or stages other than those stated in a claim. The article "a" or "an" preceding an element does not exclude the presence of a plurality of such elements. Some embodiments may be implemented by hardware including several distinct elements, and by a suitably programmed computer. In the device claim enumerating several devices, several of these devices may be embodied by one and the same item of hardware. The mere fact that certain measures are recited in mutually different dependent claims does not indicate that a combination of these measures cannot be used to advantage.

The invention claimed is:

1. A surgical robotic system for use in surgery on a subject, the surgical robotic system comprising:
an instrument manipulator for manipulating a surgical instrument held by the surgical robotic system; and
a linkage system for moveably suspending the instrument manipulator, wherein the linkage system is configured for guiding one or more suspension points of the instrument manipulator to move along respective movement trajectories to provide a movement of the instrument manipulator from a surgical position proximate to the subject to a distal position distal to the subject;
wherein the surgical robotic system includes a release mechanism for holding and releasing the instrument manipulator at the surgical position; and
wherein the movement of the instrument manipulator from the surgical position to the distal position is obtained as a result of a force acting upon the instrument manipulator when the release mechanism releases the instrument manipulator, wherein the force is generated by conversion of stored energy.

2. The surgical robotic system according to claim 1, wherein the movement of the instrument manipulator causes a tip of a distal end of the instrument manipulator to move along a tip movement trajectory, wherein an end portion of the tip movement trajectory proximate to the subject is oriented in a direction perpendicular to a surgical entry surface of the subject.

3. The surgical robotic system according to claim 2, wherein the surgical robotic system further includes a cannula connector for coupling to a cannula, wherein the cannula provides an opening at the surgical entry surface of the subject for the surgical instrument to enter an interior of the subject, and wherein the cannula connector:
is coupled to the instrument manipulator at a proximal end;
includes a through passage for allowing the surgical instrument to pass through the through passage; and
is shaped to fit a shape of the cannula so as to establish a releasable coupling with the cannula which releases when the instrument manipulator moves in the direction perpendicular to the surgical entry surface of the subject.

4. The surgical robotic system according to claim 3, wherein the cannula has a conical shape and wherein the cannula connector is conically shaped to fit the conical shape of the cannula.

5. The surgical robotic system according to claim 3, wherein the cannula connector is capable of being rigidly coupled to the cannula.

6. The surgical robotic system according to claim 1, wherein the distal position is located laterally sideways with respect to a sagittal plane of the subject and the linkage system is configured for guiding the instrument manipulator laterally sideward with respect to the sagittal plane during the movement from the surgical position to the distal position.

7. The surgical robotic system according to claim 1, wherein the distal position is located lower than the subject and the linkage system is configured for guiding the instrument manipulator downward with respect to a coronal plane of the subject during the movement from the surgical position to the distal position.

8. The surgical robotic system according to claim 1, wherein the force is generated passively by conversion of stored potential energy.

9. The surgical robotic system according to claim 8, wherein the force is generated by gravity and/or a preloaded spring.

10. The surgical robotic system according to claim 1, wherein the release mechanism includes a hook, a lock arm pin, and a release actuator, wherein:
the hook is arranged and configured for gripping the lock arm pin; the lock arm pin being connected to the linkage system or the instrument manipulator via a lock arm;
the release actuator is arranged and configured for releasing the hook from the lock arm pin.

11. The surgical robotic system according to claim 1, wherein the linkage system is provided with a manual actuation handle for enabling a user to manually actuate the linkage system so as to move a respective suspension point of the instrument manipulator along at least part of the movement trajectory.

12. The surgical robotic system according to claim 1, wherein the surgical robotic system includes an actuator for actuating the linkage system so as to move a respective suspension point of the instrument manipulator.

13. The surgical robotic system according to claim 1, wherein the linkage system includes a slider for sliding along a guide shaped to establish at least part of the movement trajectory.

14. The surgical robotic system according to claim 1, wherein the linkage system includes rod members rotatable about a respective rotation point and having different lengths.

15. The surgical robotic system according to claim 1, wherein the movement trajectory is an arc-shaped movement trajectory.

16. The surgical robotic system according to claim 1, wherein the surgical robotic system is a surgical master-slave robot.

17. The surgical robotic system according to claim 1, wherein the instrument manipulator mounts the surgical instrument.

18. The surgical robotic system according to claim 1, wherein the linkage system comprises:
a first linkage component coupled to the instrument manipulator at a first suspension point of the instrument manipulator;
a second linkage component coupled to the instrument manipulator at a second suspension point of the instrument manipulator.

19. The surgical robotic system according to claim 18, wherein
the first linkage component is configured for guiding the first suspension point of the instrument manipulator to move along a first movement trajectory;
the second linkage component is configured for guiding the second suspension point of the instrument manipulator to move along a second movement trajectory; and
wherein the first movement trajectory and the second movement trajectory differ and are selected to provide the movement as a combined translational and rotational movement of the instrument manipulator which moves the instrument manipulator along a predefined trajectory from the surgical position to the distal position.

* * * * *